(12) United States Patent
Hsieh et al.

(10) Patent No.: US 10,364,428 B2
(45) Date of Patent: Jul. 30, 2019

(54) METHODS AND KITS FOR POST-IVT RNA PURIFICATION

(71) Applicant: Corning Incorporated, Corning, NY (US)

(72) Inventors: Yi-Cheng Hsieh, Horseheads, NY (US); Cheng-I Hsu, Hsinchu (TW); Chia-Ling Wu, Tainan (TW); Hsan-Jan Yen, New Taipei (TW)

(73) Assignee: Corning Incorporated, Corning, NY (US)

( * ) Notice: Subject to any disclaimer, the term of this patent is extended or adjusted under 35 U.S.C. 154(b) by 90 days.

(21) Appl. No.: 15/526,651

(22) PCT Filed: Nov. 10, 2015

(86) PCT No.: PCT/US2015/059867
§ 371 (c)(1),
(2) Date: May 12, 2017

(87) PCT Pub. No.: WO2016/077294
PCT Pub. Date: May 19, 2016

(65) Prior Publication Data
US 2017/0314010 A1    Nov. 2, 2017

Related U.S. Application Data

(60) Provisional application No. 62/079,854, filed on Nov. 14, 2014.

(51) Int. Cl.
*C12N 15/10* (2006.01)

(52) U.S. Cl.
CPC .................... *C12N 15/1013* (2013.01)

(58) Field of Classification Search
CPC . C12N 15/1013; C12N 15/10; C12N 15/1003
See application file for complete search history.

(56) References Cited

U.S. PATENT DOCUMENTS

| | | |
|---|---|---|
| 5,705,628 A | 1/1998 | Hawkins |
| 5,898,071 A | 4/1999 | Hawkins |
| 5,981,235 A | 11/1999 | Shultz et al. |
| 6,284,470 B1 | 9/2001 | Bitner et al. |
| 6,433,160 B1 | 8/2002 | Collis |
| 6,534,262 B1 | 3/2003 | McKernan et al. |
| 6,562,568 B1 | 5/2003 | Kleiber et al. |
| 6,914,137 B2 | 7/2005 | Baker |
| 7,078,224 B1 | 7/2006 | Bitner et al. |
| 7,517,969 B2 | 4/2009 | Reitan et al. |
| 7,767,804 B2 | 8/2010 | Bair, Jr. et al. |
| 8,507,198 B2 | 8/2013 | Bost et al. |
| 8,691,969 B2 | 4/2014 | Deggerdal et al. |
| 9,062,303 B2 | 6/2015 | Chen et al. |
| 2010/0190240 A1 | 7/2010 | Jiang et al. |
| 2011/0166338 A1 | 7/2011 | Jiang et al. |
| 2012/0295328 A1* | 11/2012 | Wyrich .............. C12N 15/1003 435/219 |
| 2014/0142290 A1 | 5/2014 | Madden et al. |
| 2015/0023283 A1 | 1/2015 | Liu et al. |

FOREIGN PATENT DOCUMENTS

| | | |
|---|---|---|
| CN | 102071186 A | 5/2011 |
| EP | 1748072 A1 | 1/2007 |
| WO | 02066993 A1 | 8/2002 |
| WO | 2004108925 A1 | 12/2004 |
| WO | 2009076645 A1 | 6/2009 |

OTHER PUBLICATIONS

"Agencourt® Rnaclean® XP, In Vitro Produced RNA and cDNA Purification." Beckman Coulter, 14 Pages, 2009.
Chomczynski, P., et al., "Single-Step Method of RNA Isolation by Acid Guanidinium Thiocyanate-Phenol-Cloroform Extraction," Analytical Biochemistry, vol. 162, pp. 156-159, 1987.
Lee, H., et al., "High-Speed RNA Microextraction Technology Using Magnetic Oligo-DT Beads and Lateral Magnetophoresis." Lab on a Chip, vol. 10, No. 20, pp. 2764-2770, Sep. 2, 2010.
Freeman, L., "Geneclean®." Department of Biology, Davidson College, 3 Pages, 2000 <http://www.bio.davidson.edu/courses/Molbio/MolStudents/spring99/lauren/geneclean.html> Retrieved May 12, 2017.

(Continued)

*Primary Examiner* — Pancham Bakshi
(74) *Attorney, Agent, or Firm* — Frank Brock Riggs (57) ABSTRACT

The disclosure relates to methods for nucleic acid purification, comprising (a) combining a sample comprising at least one nucleic acid with a binding buffer comprising at least one magnetic particle and having a pH ranging from about 4 to about 10 to form a solution; (b) incubating the sample with the binding buffer for a time period sufficient to reversibly bind the at least one nucleic acid to the at least one magnetic particle to form at least one modified magnetic particle, (c) separating the at least one modified magnetic particle from the solution, (d) washing the at least one modified magnetic particle with at least one wash buffer; and (e) combining the at least one modified magnetic particle with an elution buffer Kits comprising these buffers and magnetic particles are also disclosed herein.

11 Claims, 6 Drawing Sheets

(56) References Cited

OTHER PUBLICATIONS

Chang C., et al., "Sources of Diversity in T Cell Epitope Discovery." Frontiers in Bioscience, vol. 16, pp. 3014-3035, Jun. 1, 2011.
Xu, L., et al., "Altered Nucleic Acid Partitioning During Phenol Extraction or Silica Adsorption by Guanidinium and Potassium Salts." Analytical Biochemistry, vol. 419, No. 2, pp. 309-316, Aug. 31, 2011.
Kedzierski, W., et al, "A Novel Non-Enzymatic Procedure for Removing DNA Template From RNA Transcription Mixtures." Biotechniques, vol. 10, No. 2, pp. 210-214, Feb. 10, 1991.
Filipowicz, W., et al., "Post-Transcriptional Gene Silencing by siRNAs and miRNAs." Current Opinion in Structural Biology, vol. 15, No. 3, pp. 331-341, May 31, 2005.
Boom, R., et al., "Rapid and Simple Method for Purification of Nucleic Acids." Journal of Clinical Microbiology, vol. 28, No. 3, pp. 495-503, Mar. 1990.
Berensmeier, S., "Magnetic Particles for the Separation and Purification of Nucleic Acids." Applied Microbiology and Biotechnology, vol. 73, No. 3, pp. 495-504, Oct. 25, 2016.
International Search Report and Written Opinion of the International Searching Authority; PCT/US2015/059867; dated Feb. 16, 2016; 14 Pages; European Patent Office.
EP15802247.5 Office Action dated Jan. 31, 2019, European Patent Office, 7 Pgs.

\* cited by examiner

METHODS AND KITS FOR POST-IVT RNA PURIFICATION

This is a national stage application under 35 U.S.C. § 371 of International Application No. PCT/US2015/059867, filed on Nov. 10, 2015, which claims the benefit of priority under 35 U.S.C. § 119 of U.S. Provisional Application Ser. No. 62/079,854 filed on Nov. 14, 2014 the content of which is relied upon and incorporated herein by reference in its entirety.

FIELD OF THE DISCLOSURE

The present disclosure relates generally to methods and kits for nucleic acid purification and, more particularly, to magnetic particle-based kits and methods for purifying samples containing RNA after in vitro transcription.

BACKGROUND

Nucleic acid purification, such as the isolation of DNA or RNA, can be an important step in various biochemical and diagnostic procedures. RNA can be used in many applications, such as gene expression studies, molecular studies, and/or biochemical studies, for instance, in RNA interference, microinjection, infection, in vitro translation, and/or nuclease protection assay procedures. Transcription is the first step in gene expression, in which complementary and antiparallel RNA strands are synthesized from DNA template(s) using RNA polymerase. In vitro transcription (IVT) can provide a way to in vitro transcribe nucleotides with desired sequences or modifications, such as capping or radio labels, from DNA.

There are a variety of IVT kits designed to drive transcription, e.g., for T7, T3, or SP6 promoters. However, before continuing with downstream applications, it may be necessary to purify post-IVT samples to remove one or more contaminants, such as salts, proteins, enzymes, oligonucleotides, and the like. The presence of such contaminating materials can impede or prevent many downstream processes. Thus, it can be important to effectively isolate nucleic acids from the post-IVT mixture to ensure a desired end-use functionality.

The selected method for purifying nucleic acids can, in some instances, impact various properties of the isolated product, including yield, quality, and/or purity of the nucleic acid sample. While many approaches have been developed for nucleic acid purification, these methods may have one or more drawbacks including, for example, high cost, high complexity, slow speed, low yield, low purity, contamination, toxicity, and/or inefficiency. RNA of relatively high purity can be isolated from IVT mixtures using traditional precipitation procedures, such as phenol/chloroform extraction; however, such methods can be time-consuming and complex.

Solid phase-based methods, such as methods utilizing magnetic beads, spin columns, and/or filtration systems, have been presented as an alternative solution. Among these methods, magnetic particle-based purification systems may have various advantages, such as enhanced simplicity, due to the lack of centrifugation and/or vacuum steps. However, methods employing magnetic particles can still suffer from various disadvantages, such as slow speed, high complexity, and/or poor overall yield.

Accordingly, it would be advantageous to provide magnetic particle-based methods and kits for nucleic acid purification that may be faster, less complex, less expensive, and/or improved in terms of product purity and/or yield. The resulting purified nucleic acids can be used in a wide variety of gene expression, molecular, and/or biochemical applications.

SUMMARY

The disclosure relates, in various embodiments, to methods for purifying nucleic acids, the methods comprising (a) combining a sample comprising at least one nucleic acid with a binding buffer comprising at least one magnetic particle and having a pH ranging from about 4 to about 10 to form a solution; (b) incubating the sample with the binding buffer for a time period sufficient to reversibly bind the at least one nucleic acid to the at least one magnetic particle to form at least one modified magnetic particle, (c) separating the at least one modified magnetic particle from the solution, (d) washing the at least one modified magnetic particle with at least one wash buffer; and (e) combining the at least one modified magnetic particle with an elution buffer.

According to various embodiments, the binding buffer can comprise at least one chaotropic agent, present in a concentration ranging from about 0.2 M to about 6 M, at least one alcohol, present in a concentration ranging from about 0.1 M to about 5 M, and optionally at least one salt, present in a concentration ranging from about 10 mM to about 100 mM. In other embodiments, the wash buffer can comprise at least one alcohol and optionally at least one salt. According to further embodiments, the elution buffer can be chosen from water and low-salt solutions comprising, for example, from about 0.1 mM to about 10 mM of at least one ion chelating agent and/or about 10 mM to about 100 mM of at least one buffer compound. Magnetic particles can be chosen, for example, from carboxyl coated magnetic particles, silica-based magnetic particles, and combinations thereof. Also disclosed herein are nucleic acid purification kits comprising these buffers and magnetic particles.

Additional features and advantages of the invention will be set forth in the detailed description which follows, and in part will be readily apparent to those skilled in the art from that description or recognized by practicing the invention as described herein, including the detailed description which follows, the claims, and the appended drawings.

It is to be understood that both the foregoing general description and the following detailed description present various embodiments of the disclosure, and are intended to provide an overview or framework for understanding the nature and character of the claims. The accompanying drawings are included to provide a further understanding of the disclosure, and are incorporated into and constitute a part of this specification. The drawings illustrate various embodiments of the disclosure and together with the description serve to explain the principles and operations of the invention.

BRIEF DESCRIPTION OF THE DRAWINGS

The following detailed description can be best understood when read in conjunction with the following drawings, where like structures are indicated with like reference numerals and in which.

DETAILED DESCRIPTION

Methods

Disclosed herein are methods for nucleic acid purification, the methods comprising (a) combining a sample comprising at least one nucleic acid with a binding buffer comprising at least one magnetic particle and having a pH ranging from about 4 to about 10 to form a solution; (b) incubating the sample with the binding buffer for a time period sufficient to reversibly bind the at least one nucleic acid to the at least one magnetic particle to form at least one modified magnetic particle, (c) separating the at least one modified magnetic particle from the solution, (d) washing the at least one modified magnetic particle with at least one wash buffer; and (e) combining the at least one modified magnetic particle with an elution buffer.

Embodiments of the disclosure will be discussed with reference to FIG. 1, which illustrates a flow diagram for a nucleic acid purification method according to non-limiting embodiments of the disclosure. The following general description is intended to provide an overview of the claimed methods and various aspects will be more specifically discussed throughout the disclosure with reference to the non-limiting embodiments, these embodiments being interchangeable with one another in the context of the general method discussed below.

Figure 1:
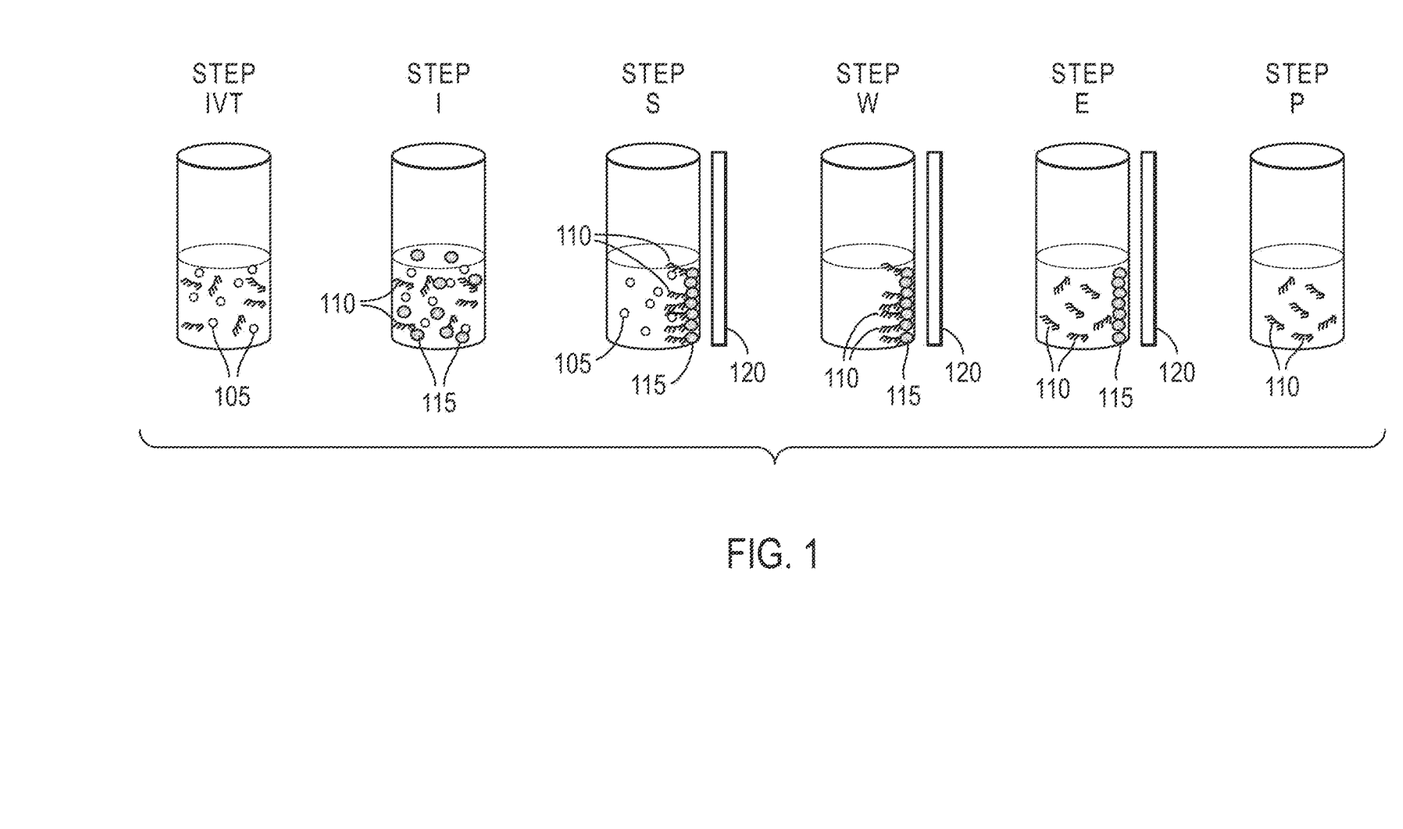
FIG. 1 is a flow diagram illustrating a nucleic acid purification method according to one embodiment of the disclosure.

As demonstrated in FIG. 1, in step IVT, a sample can be produced containing RNA molecules 110 and unwanted contaminants 105 (e.g., salts, proteins, enzymes, oligonucleotides, carbohydrates, DNA templates, and nucleotide triphosphates (NTP). In step I, the sample can be combined and incubated with a binding buffer comprising, inter alia, at least one magnetic particle 115. During incubation, RNA molecules 110 in the sample may be reversibly bound to the surface of the magnetic particles 115. A magnet 120 can then be used to attract the magnetic particles 115 and separate them from the remaining solution in step S. Unbound contaminants 105 can be removed by washing the magnetic particles 115 using one or more washing buffers in step W. The RNA 110 can then be eluted and unbound from the magnetic beads using one or more elution buffers in step E. Finally, the magnetic particles 115 can be separated from the RNA 110 in step P to produce a purified product which can then be used in a variety of applications.

As used herein, the term "sample comprising at least one nucleic acid" and variations thereof is intended to denote any material which may contain at least one nucleic acid, e.g., a DNA molecule, RNA molecule, or DNA/RNA hybrid molecule. The at least one nucleic acid can include, for example, genomic DNA, chromosomal DNA (cDNA), plasmid DNA (pDNA), total RNA, messenger RNA (mRNA), ribosomal RNA (rRNA), transfer RNA (tRNA), and/or RNA/DNA hybrids. In various embodiments, the sample can be a post-IVT mixture comprising RNA. According to additional embodiments, the at least one nucleic acid to be purified can be RNA, e.g., total RNA.

According to various methods disclosed herein, a sample comprising at least one nucleic acid, e.g., a post-IVT sample comprising RNA, can be combined with a binding buffer (B1) (see, e.g., step B in FIG. 1). The binding buffer B1 can comprise at least one chaotropic agent (C1), at least one alcohol (A1), and optionally at least one salt (Z1). A volumetric ratio between the sample and the binding buffer B1 can range, for example, from about 1:1.5 to about 1:3, such as from about 1:1.8 to about 1:2.5, or from about 1:2 to about 1:2.2, including all ranges and subranges therebetween. In certain embodiments, the volumetric ratio between the sample and binding buffer can be about 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, or 1:3, including all ranges and subranges therebetween.

The sample and the binding buffer B1 can be combined in any manner known in the art, for example, the binding buffer B1 can be added to the sample and mixed, e.g., by inversion. In certain embodiments, the mixture may be inverted multiple times, such as at least five times, at least ten times, or more. The sample can be incubated in the binding buffer B1 for a period of time sufficient to bind the at least one nucleic acid to the at least one magnetic particle. This time period can range, for example, from about 1 minute to about 30 minutes, such as from about 2 minutes to about 25 minutes, from about 3 minutes to about 20 minutes, from about 4 minutes to about 15 minutes, or from about 5 minutes to about 10 minutes, including all ranges and subranges therebetween.

The at least one chaotropic agent C1 can be present in the binding buffer B1 in a concentration ranging, for example, from about 0.2 M to about 6 M, such as from about 0.3 M to about 5 M, from about 0.5 M to about 4 M, from about 0.7 M to about 3.5 M, from about 1 M to about 3 M, from about 1.2 M to about 2.5 M, or from about 1.5 M to about 2 M, including all ranges and subranges therebetween. For example, the C1 concentration can be about 0.2 M, 0.3 M, 0.4 M, 0.5 M, 0.6 M, 0.7 M, 0.8 M, 0.9 M, 1 M, 1.1 M, 1.2 M, 1.3 M, 1.4 M, 1.5 M, 1.6 M, 1.7 M, 1.8 M, 1.9 M, 2 M, 2.1 M, 2.2 M, 2.3 M, 2.4 M, 2.5 M, 2.6 M, 2.7 M, 2.8 M, 2.9 M, 3 M, 3.1 M, 3.2 M, 3.3 M, 3.4 M, 3.5 M, 3.6 M, 3.7 M, 3.8 M, 3.9 M, 4 M, 4.1 M, 4.2 M, 4.3 M, 4.4 M, 4.5 M, 4.6 M, 4.7 M, 4.8 M, 4.9 M, 5 M, 5.1 M, 5.2 M, 5.3 M, 5.4 M, 5.5 M, 5.6 M, 5.7 M, 5.8 M, 5.9 M, or 6 M, including all ranges and subranges therebetween. According to various embodiments, the at least one chaotropic agent C1 can be chosen from guanidine salts, such as hydrochloride (GuHCl) and guanidium thiocyanate (GuSCN); lithium salts, such as lithium acetate and lithium perchlorate; and combinations thereof. In certain non-limiting embodiments, the at least one chaotropic agent C1 can be chosen from GuHCl and GuSCN. The at least one chaotropic agent C1 may, in various embodiments, be used to promote binding of the at least one nucleic acid to the at least one magnetic particle.

The at least one alcohol A1 can be present in the binding buffer B1 in a concentration ranging, for example, from about 0.1 M to about 5 M, such as from about 0.3 M to about 4.5 M, from about 0.5 M to about 4 M, from about 0.7 M to about 3.5 M, from about 1 M to about 3 M, from about 1.2 M to about 2.5 M, or from about 1.5 M to about 2 M, including all ranges and subranges therebetween. For example, the A1 concentration can be about 0.1 M, 0.2 M, 0.3 M, 0.4 M, 0.5 M, 0.6 M, 0.7 M, 0.8 M, 0.9 M, 1 M, 1.1 M, 1.2 M, 1.3 M, 1.4 M, 1.5 M, 1.6 M, 1.7 M, 1.8 M, 1.9 M, 2 M, 2.1 M, 2.2 M, 2.3 M, 2.4 M, 2.5 M, 2.6 M, 2.7 M, 2.8 M, 2.9 M, 3 M, 3.1 M, 3.2 M, 3.3 M, 3.4 M, 3.5 M, 3.6 M, 3.7 M, 3.8 M, 3.9 M, 4 M, 4.1 M, 4.2 M, 4.3 M, 4.4 M, 4.5 M, 4.6 M, 4.7 M, 4.8 M, 4.9 M, or 5 M, including all ranges and subranges therebetween.

In non-limiting embodiments, the at least one alcohol A1 can make up from about 20% to about 50% by volume of the total volume of the binding buffer B1, for example, from about 25% to about 45%, or from about 30% to about 40% by volume, including all ranges and subranges therebetween. According to various embodiments, the at least one alcohol A1 can be chosen from isopropanol, ethanol, methanol, butanol, and combinations thereof. In some embodiments, the at least one alcohol A1 can be isopropanol. The at least one alcohol A1 may, in various embodiments, be chaotropic, and may be utilized to denature proteins in the sample.

The at least one salt Z1, if present, can be present in the binding buffer B1 in a concentration ranging, for example, from about 10 mM to about 100 mM, such as from about 20 mM to about 90 mM, from about 30 mM to about 80 mM, from about 40 mM to about 70 mM, or from about 50 mM to about 60 mM, including all ranges and subranges therebetween. For example, the Z1 concentration can be about 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM, including all ranges and subranges therebetween. According to various embodiments, the at least one salt Z1 can be chosen from phosphates such as monosodium phosphate ($NaH_2PO_4$), disodium phosphate ($Na_2HPO_4$), and combinations thereof.

According to various embodiments, the binding buffer B1 can have a pH ranging from about 4 to about 10, such as from about 4.5 to about 9.5, from about 5 to about 9, from about 5.5 to about 8.5, from about 6 to about 8, or from about 6.5 to about 7.5 including all ranges and subranges therebetween. For instance, the pH of the binding buffer B1 can be about 4, 4.1, 4.2, 4.3, 4.4, 4.5, 4.6, 4.7, 4.8, 4.9, 5, 5.1 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10, including all ranges and subranges therebetween.

As used herein the term "magnetic particle" and variations thereof is intended to denote a particle with a magnetic, e.g., paramagnetic or superparamagnetic, core coated with at least one material having a surface to which nucleic acid can reversibly bind. Suitable magnetic particles can include, for example, carboxyl coated paramagnetic particles, silica-based paramagnetic particles, and the like. Silica-based magnetic particles can comprise, in some embodiments, a paramagnetic core coated with siliceous oxide, thus providing a hydrous siliceous oxide adsorptive surface to which nucleic acid can bind (e.g., a surface comprising silanol groups). The magnetic particles can, in additional embodiments, be surface-modified to produce functionalized surfaces, such as weakly or strongly positively charged, weakly or strongly negatively charged, or hydrophobic surfaces, to name a few.

Non-limiting examples of commercially available magnetic particles include Qbeads from MagQu Co. Ltd., Grace beads from W. R. Grace & Co., and the like. The magnetic particles can have any size suitable for binding nucleic acid, including commercially available sizes, such as a diameter ranging from about 0.3 µm to about 10 µm in diameter, e.g., about 0.3, 0.5, 1, 2, 3, 4, 5, 6, 7, 8, 9, or 10 µm in diameter, including all ranges and subranges therebetween. Qbeads can, for example, have an average diameter ranging from about 4 µm to about 5 µm, Grace beads can have an average diameter ranging from about 5 µm to about 10 µm.

The at least one magnetic particle can be present in the binding buffer in a concentration ranging, for instance, from about 0.5 µg/µl to about 60 µg/µl, such as from about 0.75 µg/µl to about 55 µg/µl, from about 1 µg/µl to about 50 µg/µl, from about 2 µg/µl to about 45 µg/µl, from about 3 µg/µl to about 40 µg/µl, from about 4 µg/µl to about 35 µg/µl, from about 5 µg/µl to about 30 µg/µl, from about 6 µg/µl to about 25 µg/µl, from about 7 µg/µl to about 20 µg/µl, from about 8 µg/µl to about 15 µg/µl, or from about 9 µg/µl to about 10 µg/µl, including all ranges and subranges therebetween. By way of non-limiting embodiment, the at least one magnetic particle may be chosen from Qbeads and may be present in the binding buffer B1 in a concentration ranging from about 0.5 µg/µl to about 5 µg/µl. In alternative embodiments, the at least one magnetic particle may be chosen from Grace beads and may be present in the binding buffer B1 in a concentration ranging from about 2 µg/µl to about 60 µg/µl.

Without wishing to be bound by theory, it is believed that the relatively high concentration of chaotropic agent(s), alcohol(s), and/or salt(s) introduced by the binding buffer B1 can enhance the ability of nucleic acid, such as RNA, to reversibly (e.g., non-covalently) bind to the surface of the magnetic particle, such as a silica surface. The magnetic particles thus modified, e.g., comprising reversibly bound nucleic acid, can then be separated from the unbound contaminants (see, e.g., step S in FIG. 1). For instance, a magnet can be placed in proximity to the modified magnetic particles and used to draw the particles together, e.g., to form an aggregate or pellet. In certain embodiments, a container, such as a tube, containing a combined solution comprising the modified magnetic particles, can be placed on a magnetic stand, which can gather and somewhat immobilize the particles while the remaining solution is removed.

Upon binding the nucleic acid to the magnetic particles and after separation of the modified magnetic particles using a magnet, the particles can then be combined, rinsed, or washed with one or more wash buffers (see, e.g., step W in FIG. 1). A wash buffer (W1) can comprise, for example, at least one alcohol (A2) and optionally at least one salt (Z2). The modified magnetic particles can be rinsed once or multiple times with the wash buffer W1, and any additional washing can employ the same or different compositions, concentrations, and/or volumetric amounts.

The at least one alcohol A2 can be present in the wash buffer W1 in a concentration ranging, for example, from about 70% to 100% by volume, such as from about 75% to about 95%, or from about 80% to about 90% by volume, including all ranges and subranges therebetween. For example, the A2 concentration can be about 70%, 75%, 80%, 85%, 90%, 95%, or 100%, including all ranges and subranges therebetween. According to various embodiments, the at least one alcohol A2 can be chosen from isopropanol, methanol, ethanol, butanol, and combinations thereof. In certain non-limiting embodiments, the at least one alcohol A2 can be ethanol.

The at least one salt Z2, if present, can be present in the wash buffer W1 in a concentration ranging, for example, from about 10 mM to about 100 mM, such as from about 20 mM to about 90 mM, from about 30 mM to about 80 mM, from about 40 mM to about 70 mM, or from about 50 mM to about 60 mM, including all ranges and subranges therebetween. For example, the Z2 concentration can be about 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM, including all ranges and subranges therebetween. According to various embodiments, the at least one salt Z2 can be chosen from ammonium sulfate (($NH_4$)$_2SO_4$), ammonium acetate ($NH_4Ac$), lithium acetate (LiAc), potassium acetate (KAc), sodium acetate (NaAc), sodium chloride (NaCl), and combinations thereof. In certain non-limiting embodiments, the at least one salt Z2 can be chosen from NaAC and $NH_4AC$.

According to various embodiments, the pH of the wash buffer W1 can range, for example, from about 4 to about 8, such as from about 5 to about 7, from about 6 to about 6.5, or from about 6.4 to about 6.8, including all ranges and subranges therebetween. The pH of the wash buffer W1 can be adjusted by varying the amount of alcohol and/or salt, or can be adjusted using one or more buffer compounds, such as glacial acetic acid or NaOH, as disclosed herein.

After the addition and removal of the wash buffer W1, modified magnetic particles with nucleic acid reversibly bound to the surface may be provided, which can be free or substantially free of contaminants such as salts, proteins, enzymes, etc. According to various embodiments, the modified magnetic particles thus produced can then be combined with one or more elution buffers (E1) to release the bound nucleic acid and separate it from the magnetic particles (see, e.g., step E in FIG. 1). The modified magnetic particles can be incubated in the elution buffer E1 for a period of time sufficient to release the nucleic acids, such as from about 30 seconds to about 10 minutes, for example, from about 45 seconds to about 9 minutes, from about 1 minute to about 8 minutes, from about 2 minutes to about 7 minutes, from about 3 minutes to about 6 minutes, or from about 4 minutes to about 5 minutes, including all ranges and subranges therebetween. The elution buffer E1 can comprise, for example, water or a relatively low-salt solution comprising, for instance, from about 1 mM to about 10 mM of at least one buffer (e.g., Tris and the like), from about 1 mM to about 10 mM of at least one salt, and/or from about 0.1 mM to about 10 mM of at least one ion chelating agent (e.g., EDTA and the like). According to non-limiting embodiments, the elution buffer E1 can comprise about 1 mM of EDTA and about 10 mM of Tris.

The magnetic particles (no longer attached to the nucleic acid) can subsequently be removed from the solution, e.g., separated using a magnet, yielding a purified nucleic acid in solution as the final product (see, e.g., step P in FIG. 1). For example, the methods and kits disclosed herein can be used to provide a purified RNA product. According to various embodiments, the methods and kits disclosed herein can be used to efficiently produce purified RNA in a short time period. For instance, in non-limiting embodiments, the methods disclosed herein can be carried out in a time period of less than about 30 minutes, such as less than about 20 minutes. The methods disclosed herein can, in certain embodiments, provide a relative RNA yield of at least about 90% in approximately 20 minutes.

It is to be understood that the components of the various buffer solutions can, in some embodiments, be used interchangeably, e.g., can be the same or different from each other. For instance, alcohols A1 and A2 and salts Z1 and Z2, respectively, can be identical or different. Likewise, the concentrations of these components can vary and can, in some instances be identical or similar, depending on the desired application.

It is also to be understood that the methods disclosed herein can further comprise additional steps known in the art, such as centrifugation, filtration, and the like. In other non-limiting embodiments, the methods disclosed herein do not include any centrifugation or filtration steps, which may enhance the ability to automate the process. Other optional steps can include air drying, e.g., after rinsing the modified magnetic particles with wash buffer W1, the particles may be air dried for a period of time ranging from about 1 minute to about 10 minutes, such as from about 2 minutes to about 9 minutes, from about 3 minutes to about 8 minutes, from about 4 minutes to about 7 minutes, or from about 5 minutes to about 6 minutes, including all ranges and subranges therebetween. Removal and/or transfer of the various samples, solutions, or portions of the samples or solutions to new containers, such as tubes, can also be carried out during the methods disclosed herein as desired or necessary.

Kits

The disclosure also relates to kits for nucleic acid purification, the kits comprising a binding buffer, a wash buffer, and an elution buffer. The buffers can correspond, in various embodiments, to the buffers B1, W1, and E1, as disclosed above with reference to the purification methods. It should be understood that the various embodiments discussed above with respect to each of the buffers can be combined in any manner and without limitation to form the kits disclosed herein.

According to various embodiments, each buffer can be supplied in the kit with predetermined concentrations for each component that are ready-to-use. Alternatively, one or more concentrated solutions can be provided, to be diluted by the end user with the appropriate type and amount of solvent to produce the ready-to-use buffers. For example, in certain embodiments, a concentrated binding buffer can be provided in the kit, which can be diluted by the user with an alcohol, e.g., isopropanol up to a 1:1 volumetric ratio. According to further embodiments, a concentrated wash buffer W1 can be provided, which can be diluted by the user with an alcohol, such as ethanol, e.g., to a final concentration of 70% or greater by volume of ethanol. The kit can, in some embodiments, further include instructions to the end user regarding the purification protocol and/or any dilution instructions. According to other embodiments, the kit can further comprise various additional components or equipment, such as a magnetic stand, tubes, centrifuge, and/or solvents.

It will be appreciated that the various disclosed embodiments may involve particular features, elements or steps that are described in connection with that particular embodiment. It will also be appreciated that a particular feature, element or step, although described in relation to one particular embodiment, may be interchanged or combined with alternate embodiments in various non-illustrated combinations or permutations.

It is also to be understood that, as used herein the terms "the," "a," or "an," mean "at least one," and should not be limited to "only one" unless explicitly indicated to the contrary. Thus, for example, reference to "a buffer" includes examples having two or more such "buffers" unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Other than in the Examples, all numerical values expressed herein are to be interpreted as including "about," whether or not so stated, unless expressly indicated otherwise. It is further understood, however, that each numerical value recited is precisely contemplated as well, regardless of whether it is expressed as "about" that value. Thus, "a concentration greater than 2 M" and "a concentration greater than about 2 M" both include embodiments of "a concentration greater than about 2 M" as well as "a concentration greater than 2 M."

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a buffer that comprises A+B+C include embodiments where a buffer consists of A+B+C, and embodiments where a buffer consists essentially of A+B+C.

It will be apparent to those skilled in the art that various modifications and variations can be made to the present disclosure without departing from the spirit and scope of the disclosure. Since modifications combinations, sub-combinations and variations of the disclosed embodiments incorporating the spirit and substance of the disclosure may occur to persons skilled in the art, the disclosure should be construed to include everything within the scope of the appended claims and their equivalents.

The following Examples are intended to be non-restrictive and illustrative only, with the scope of the invention being defined by the claims.

EXAMPLES

Exemplary Purification Protocol

For purposes of discussion only, an exemplary protocol for purifying RNA from a sample, e.g., an IVT sample, is provided below. Of course, this protocol is not intended to be and should not be construed as limiting on the appended claims.

a) binding buffer preparation: resuspend concentrated binding buffer B1 in alcohol using a 1:1 volumetric ratio;
b) wash buffer preparation: add alcohol to concentrated wash buffer to a final volumetric concentration of 70%;
c) RNA binding: for X volume of sample, add 3× volume of the binding buffer B1, mix well, and incubate for 5 minutes;
d) separation of RNA-bound magnetic particles: magnetically separate magnetic particles with reversibly bound RNA using a magnetic stand until liquid is substantially clear and remove the clear liquid;
e) washing of RNA-bound magnetic particles: wash magnetic particles comprising reversibly bound RNA once with 700 µl of wash buffer W1;
f) removal of wash buffer: magnetically separate magnetic particles with reversibly bound RNA using a magnetic stand until liquid is substantially clear and remove the clear liquid;
g) repeat: step e) with 400 µl of wash buffer W1;
h) repeat: step f);
i) drying: allow magnetic particles with reversibly bound RNA to air dry on magnetic stand for 5-10 minutes;
j) elution of RNA: remove tube from magnetic stand and add desired volume of elution buffer E1 (more or less to produce the desired sample concentration) and incubate for at least 2 minutes at room temperature; and
k) purification of RNA: place tube on a magnetic stand to separate magnetic particles until liquid is substantially clear and remove and save clear liquid.

Comparative Example 1

Figure 2:
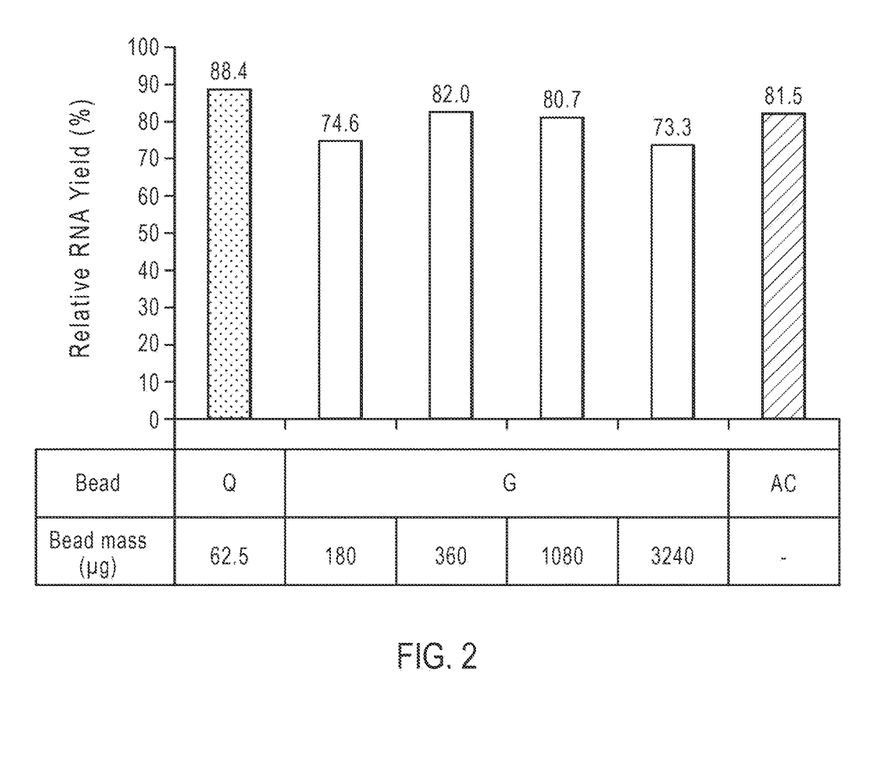
FIG. 2 is a graph illustrating RNA yield for methods according to various embodiments of the disclosure as compared to a prior art method.

A sample containing RNA was purified using the above protocol with Qbeads (62.5 µg) or Grace beads (180, 360, 1080, 3240 µg). The same sample was also purified using the Agencourt® RNAClean XP kit by Beckman Coulter. The average total RNA yield for each method was quantified and is presented in FIG. 2. The relative total RNA yield for the inventive method employing Qbeads was 88.4%. The relative total RNA yield for the inventive method employing Grace beads ranged from 73.3% (3240 µg) to 82.0% (360 µg). The comparative Agencourt® kit yielded 81.5% RNA.

Figure 3:
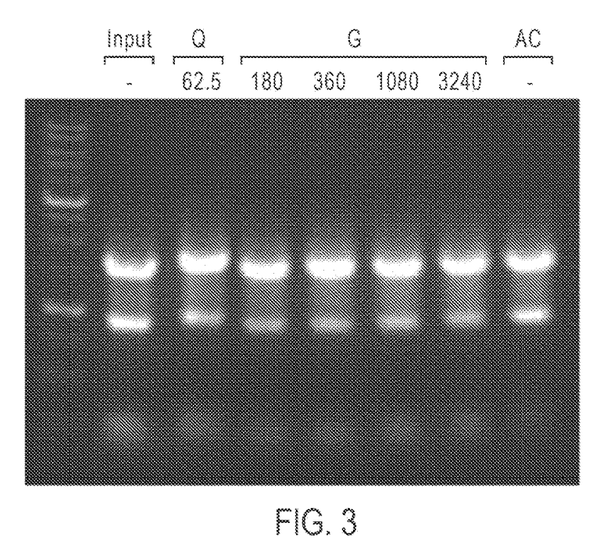
FIG. 3 illustrates an agarose gel electrophoresis analysis of RNA purified using methods according to various embodiments of the disclosure and using a prior art method.

FIG. 3 demonstrates the agarose gel electrophoresis analysis of the RNA samples for the various methods, illustrating that the quality of RNA produced by each method was comparable. Accordingly, FIGS. 2-3 demonstrate that the inventive methods, which were carried out in about 20 minutes, provide RNA yield and quality comparable to that of the benchmark comparative Agencourt® kit.

Comparative Example 2

RNA was purified using the above exemplary protocol with binding buffers B1 at varying pH (4.3 and 6.3) and varying RNA concentrations (20 µg RNA dissolved in 20 µl or in 200 µg solution). The same sample was also purified using the Agencourt® RNAClean XP kit by Beckman Coulter. The relative total RNA yield for each method was quantified and is presented in FIG. 4. The relative total RNA yield for the inventive methods employing a binding buffer at pH 4.3 was improved as compared to methods employing a binding buffer at pH 6.3. Additionally, the relative total RNA yield for inventive methods employing 20 µg/20 µl RNA was improved as compared to methods employing 20 µg/200 µl RNA.

Figure 4:
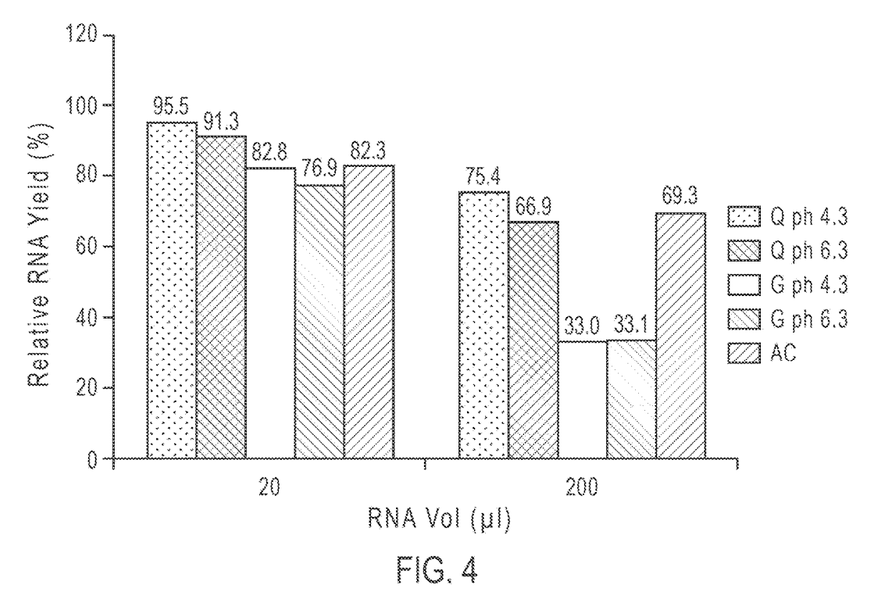
FIG. 4 is a graph illustrating RNA yield for methods according to various embodiments of the disclosure as compared to a prior art method.
Figure 5A:
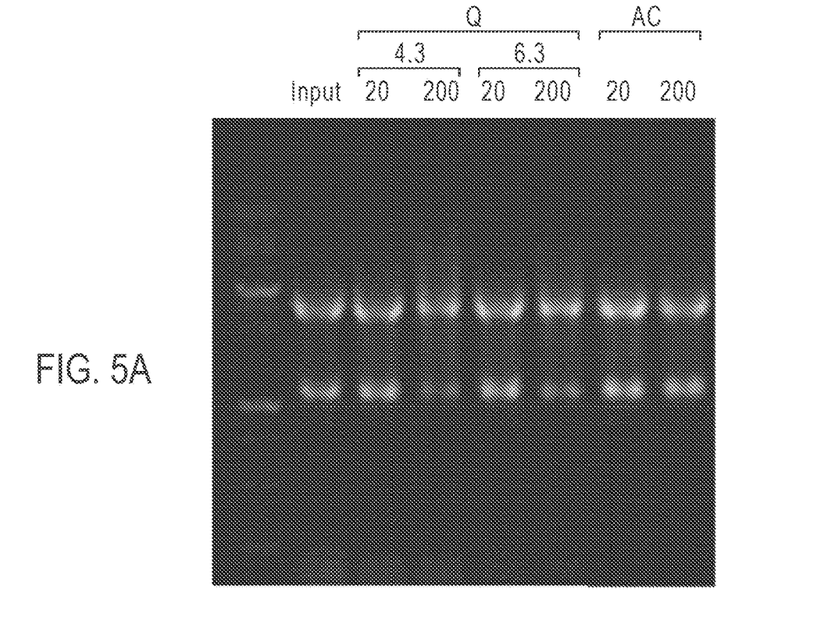
FIGS. 5A-B illustrate agarose gel electrophoresis analyses of RNA purified using methods according to various embodiments of the disclosure and using a prior art method.
Figure 5B:
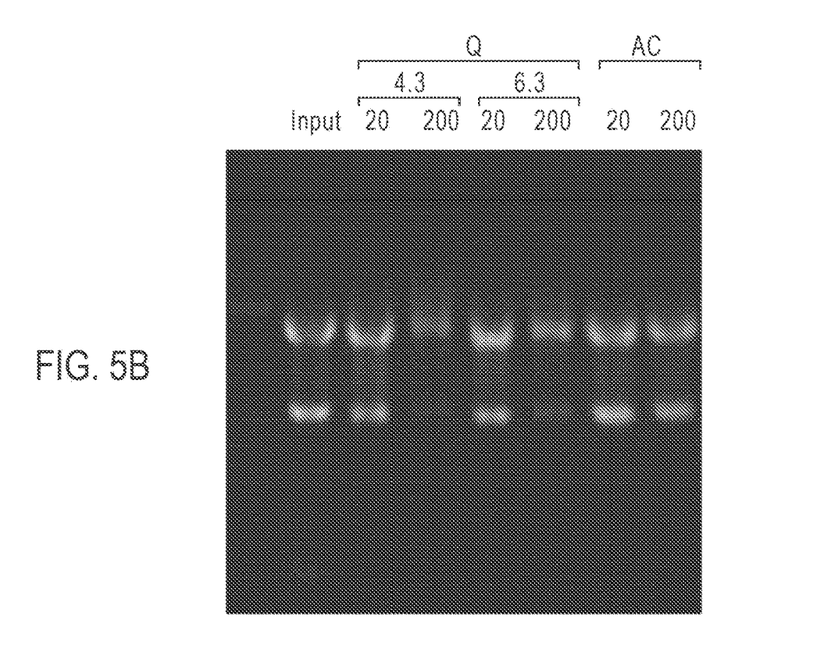

FIG. 5 demonstrates the agarose gel electrophoresis analysis of the RNA samples for the various methods, illustrating that the quality of RNA produced by inventive methods employing a binding buffer at pH 4.3 was reduced as compared to inventive methods employing a binding buffer at pH 6.3. FIGS. 4-5 thus demonstrate that the inventive methods, which were carried out in about 20 minutes, provide RNA yield and/or quality that is improved over or comparable to that of the benchmark comparative Agencourt® kit.

Comparative Example 3

RNA was purified from an IVT sample using the above exemplary protocol with Qbeads (62.5 μg) or Grace beads (360 μg). The same sample was also purified using the Agencourt® RNAClean XP kit by Beckman Coulter. The RNA yield for each method was quantified and is presented in FIG. 6, with results normalized relative to the Agencourt® yield. The relative total RNA yield for the inventive method employing Qbeads was 96.0%. The relative total RNA yield for the inventive method employing Grace beads was 91.2%.

Figure 7:
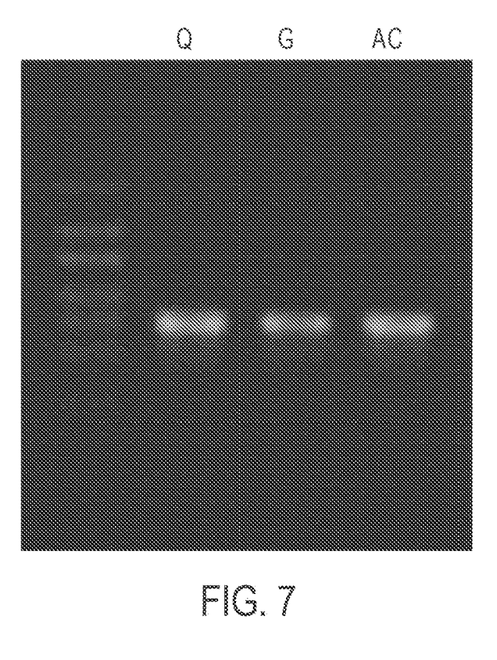
FIG. 7 illustrates an agarose gel electrophoresis analysis of nucleic acid purified using methods according to various embodiments of the disclosure and using a prior art method.
Figure 8:
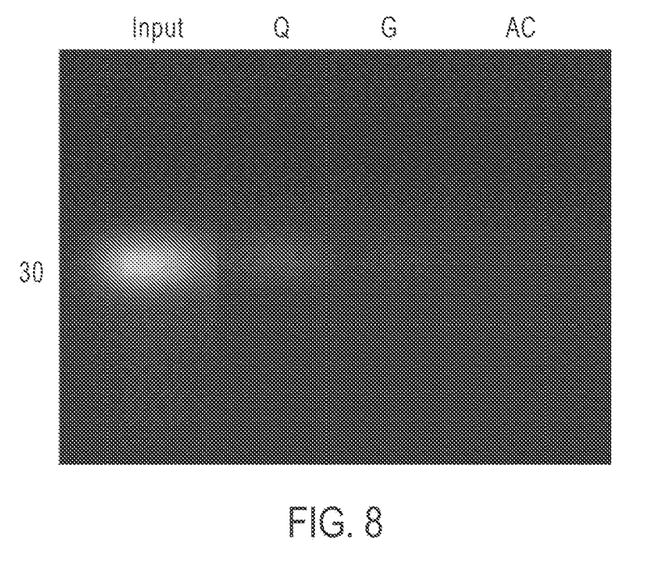
FIG. 8 illustrates an agarose gel electrophoresis analysis of small nucleic acid fragments purified using methods according to various embodiments of the disclosure and using a prior art method.

FIG. 7 demonstrates the agarose gel electrophoresis analysis of the nucleic acid samples for the various methods, illustrating that the quality of nucleic acid produced by each method was comparable. FIG. 8 demonstrates the agarose gel electrophoresis analysis for oligonucleotides (30 nt), illustrating that the ability of the inventive methods to bind small fragment nucleic acids is improved over that of the comparative Agencourt® method.

Figure 6:
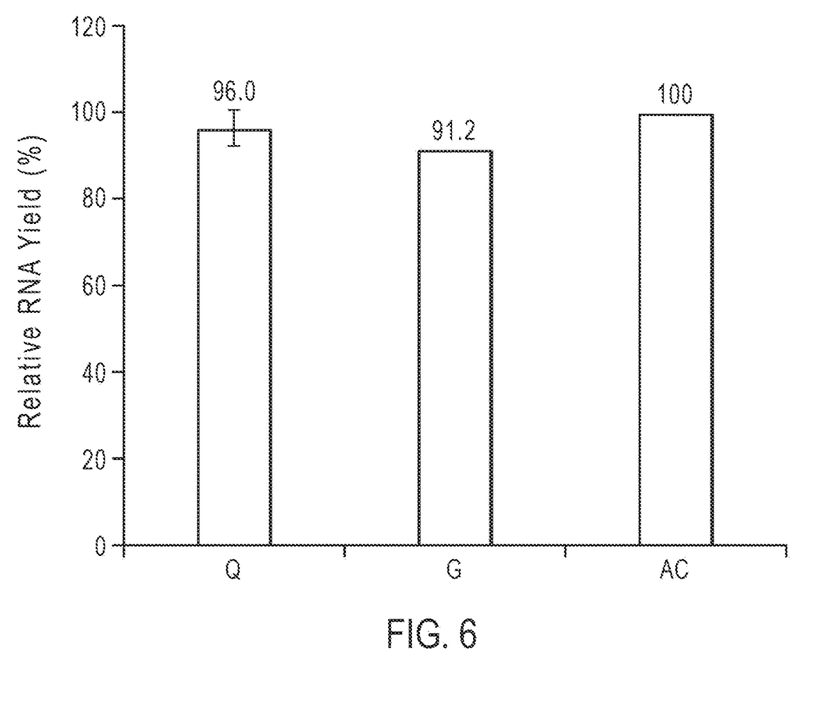
FIG. 6 is a graph illustrating RNA yield for methods according to various embodiments of the disclosure as compared to a prior art method.

Accordingly, FIGS. 6-8 demonstrate that the inventive methods, which were carried out in about 20 minutes, provide RNA yield and quality comparable to that of the benchmark comparative Agencourt® kit, while also providing improved small nucleic acid fragment binding.

What is claimed is:

1. A method for nucleic acid purification, comprising:
   (a) combining a sample comprising at least one nucleic acid with a binding buffer having a pH ranging from about 4 to about 10 to form a solution;
   wherein the binding buffer comprises at least one magnetic particle, at least one chaotropic agent, present in a concentration ranging from about 0.2 M to about 6 M, at least one first alcohol, present in a concentration ranging from about 0.1 M to about 5 M, and at least one first salt, present in a concentration ranging from about 10 mM to about 100 mM;
   (b) incubating the solution for a time period sufficient to reversibly bind the at least one nucleic acid to the at least one magnetic particle to form at least one modified magnetic particle;
   (c) separating the at least one modified magnetic particle from the combined solution;
   (d) washing the at least one modified magnetic particle with at least one wash buffer comprising at least one second alcohol and optionally at least one second salt; and
   (e) combining the at least one modified magnetic particle with an elution buffer.

2. The method of claim 1, wherein the sample comprising the at least one nucleic acid is an in vitro transcription (IVT) sample comprising RNA.

3. The method of claim 1, wherein the at least one first chaotropic agent is chosen from guanidine hydrochloride (GuHCl), guanidium thiocyanate (GuSCN), lithium salts, and combinations thereof,
   wherein the at least one first alcohol is chosen from isopropanol, methanol ethanol, butanol, and combinations thereof, and
   wherein the at least one first salt is chosen from monosodium phosphate, disodium phosphate, and combinations thereof.

4. The method of claim 1, wherein the at least one second alcohol is chosen from isopropanol, methanol, ethanol, butanol, and combinations thereof, and
   wherein the at least one second salt is chosen from ammonium sulfate (($NH_4)_2SO_4$), ammonium acetate ($NH_4Ac$), lithium acetate (LiAc), potassium acetate (KAc), sodium acetate (NaAc), sodium chloride (NaCl), and combinations thereof.

5. The method of claim 1, wherein the wash buffer comprises at least about 70% by volume of the at least one second alcohol.

6. The method of claim 1, wherein the at least one magnetic particle is chosen from carboxyl coated paramagnetic particles, silica-based paramagnetic particles, and combinations thereof.

7. The method of claim 1, wherein the at least one magnetic particle is present in the binding buffer in a concentration ranging from about 0.5 μg/μl to about 60 μg/μl.

8. The method of claim 1, wherein the incubation time period ranges from about 1 minute to about 30 minutes.

9. The method of claim 1, wherein the volumetric ratio of the sample containing the at least one nucleic acid to the binding buffer ranges from about 1:1.5 to about 1:3.

10. The method of claim 1, wherein the elution buffer is chosen from water and solutions comprising at least one buffer compound and/or at least one ion chelating agent.

11. The method of claim 1, wherein the at least one modified magnetic particle is incubated with the elution buffer for a time period ranging from about 30 seconds to about 10 minutes.

* * * * *

UNITED STATES PATENT AND TRADEMARK OFFICE
CERTIFICATE OF CORRECTION

PATENT NO. : 10,364,428 B2
APPLICATION NO. : 15/526651
DATED : July 30, 2019
INVENTOR(S) : Yi-Cheng Hsieh et al.

It is certified that error appears in the above-identified patent and that said Letters Patent is hereby corrected as shown below:

On the Title Page

In Column 2, item (56), other publications, Line 4, delete "Thiocyanate-Phenol-Cloroform" and insert -- Thiocyanate-Phenol-Chloroform --, therefor.

Signed and Sealed this
Tenth Day of December, 2019

Andrei Iancu
*Director of the United States Patent and Trademark Office*